US005609617A

United States Patent [19]
Shealy et al.

[11] Patent Number: 5,609,617
[45] Date of Patent: Mar. 11, 1997

[54] METHOD FOR ENHANCEMENT OF DEHYDROEPIANDROSTERONE

[75] Inventors: C. Norman Shealy, Rte. 1, Box 216, Fair Grove, Mo. 65648; Saul Liss, Hawthorne, N.J.; Caroline M. Myss, Melrose Park, Ill.; Roger K. Cady, Springfield, Mo.

[73] Assignee: C. Norman Shealy, Fair Grove, Mo.

[21] Appl. No.: 390,965

[22] Filed: Feb. 21, 1995

[51] Int. Cl.⁶ ........................................... A61N 1/36
[52] U.S. Cl. ............................................... 607/68
[58] Field of Search .......................... 607/2, 68, 69, 607/76

[56] References Cited

U.S. PATENT DOCUMENTS

| | | |
|---|---|---|
| 3,850,161 | 11/1974 | Liss . |
| 3,902,502 | 9/1975 | Liss et al. . |
| 4,518,595 | 5/1985 | Coleman et al. . |
| 4,550,733 | 11/1985 | Liss et al. . |
| 4,559,948 | 12/1985 | Liss et al. . |
| 4,574,808 | 3/1986 | Liss et al. . |
| 4,586,509 | 5/1986 | Liss et al. . |
| 4,614,193 | 9/1986 | Liss et al. . |
| 4,627,438 | 12/1986 | Liss et al. . |
| 4,628,052 | 12/1986 | Peat . |
| 4,784,142 | 11/1988 | Liss et al. . |
| 4,835,147 | 5/1989 | Roberts . |
| 4,844,075 | 7/1989 | Liss et al. . |
| 4,856,526 | 8/1989 | Liss et al. . |
| 4,920,115 | 4/1990 | Nestler et al. . |
| 5,077,284 | 12/1991 | Loria et al. . |
| 5,109,847 | 5/1992 | Liss et al. . |
| 5,110,810 | 5/1992 | Eich et al. . |
| 5,162,198 | 11/1992 | Eich et al. . |

OTHER PUBLICATIONS

S. Kent, "DHEA: 'Miracle' drug?", Geriatrics for the Primary Care Physician, vol. 37, No. 9, 1982, pp. 157–159.
N. Orentreich, et al., "Age Changes and Sex Differences in Serum Dehydroepiandrosterone Sulfate Concentrations throughout Adulthood", The Journal of Clinical Endocrinology & Metabolism, vol. 59, No. 3, 1984, pp. 551–555.
E. Barrett–Connor, et al., "A Prospective Study of Dehydroepiandrosterone Sulfate, Mortality, and Cardiovascular Disease", The New England Journal of Medicine, vol. 315, No. 24, 1986, pp. 1519–1524.
G. B. Gordon, et al., "Reduction of Atherosclerosis by Administration of Dehydroepiandrosterone", The Journal of Clinical Investigation, vol. 82, No. 2, 1988, pp. 712–720.
W. Regelson, et al., "Hormonal Intervention: 'Buffer Hormones' or 'State Dependency'", vol. 518, 1988, pp. 260–273.
Y. Arad, et al., "Dehydroepiandrosterone Feeding Prevents Aortic Fatty Streak Formation and Accumulation in Cholesterol–fed Rabbit", Arteriosclerosis, vol. 9, No. 2, 1989, pp. 159–166.
S. Liss, Cranial Stimulator, Professional Instrument Instruction Manual, pp. 1–11, 1994.

Primary Examiner—William E. Kamm
Attorney, Agent, or Firm—Foley & Lardner

[57] ABSTRACT

A method for enhancing serum dehydroepiandrosterone (DHEA) levels in human beings resulting in improved host response to infection and resistance to pathogenic and opportunistic infectious organisms. The serum concentration of DHEA is elevated through the use of topically applied preparations containing the steroid, progesterone, through two different types of electronic stimulators applied to specific acupuncture points on an individual's body, or by combination of the two methods. One or more of the methods may be applicable to the whole.

12 Claims, 8 Drawing Sheets

CARRIER FREQUENCY
15,000 hz MONOPOLAR

FIG. 6A

1st MODULATOR
15 hz      FIG. 6B

2nd MODULATOR
500 hz     FIG. 6C

TYPICAL COMBINED
WAVEFORM (MONOPOLAR)

FIG. 6D

TYPICAL COMBINED
WAVEFORM (BIPOLAR)

METHOD FOR ENHANCEMENT OF DEHYDROEPIANDROSTERONE

FILED OF THE INVENTION

This invention pertains to a method for enhancing serum levels of dehydroepiandrosterone in human beings without administration of exogenous dehydroepiandrosterone or salts thereof.

BACKGROUND OF THE INVENTION

Dehydroepiandrosterone, also known as prasterone, 3-hydroxyandrost-5-en-17-one, dehydroisoandrosterone, trans-dehydroandrosterone, or $\Delta^5$-androsten-3-$\beta$ol-17-one (referred to hereinafter as "DHEA"), is a 17-ketosteroid, which is quantitatively one of the major adrenocortical steroid hormones present in the metabolism of humans and other mammals. S. Budavari, ed., Merck Index, Eleventh Edition (1989). This endogenous androgenic steroid has been shown to have a myriad of biological activities. An assortment of prior art has recognized the plethora of beneficial effects of DHEA, its sulfate ester (DHEA-S) and salts thereof. DHEA is readily interconvertible in vivo with DHEA-S through the action of intracellular sulfatases.

In U.S. Pat. No. 4,920,115 to Nestler et al., oral dosages of DHEA given to healthy male individuals were shown to reduce body fat mass, increase muscle mass, lower LDL cholesterol levels without affecting HDL cholesterol levels, and not affect tissue sensitivity to insulin in human patients. Nestler et al. described the use of pharmaceutical preparations of DHEA as a preventative means to avoid development of atherosclerosis.

U.S. Pat. Nos. 5,110,810 and 5,162,198 issued to Eich et al., disclose methods for treating human beings with pharmacological quantities of DHEA, resulting in increased serum DHEA and DHEA-S in their blood, which lowers rates of platelet aggregation. By reducing the rate of platelet aggregation, the incidence of morbidity and mortality from vascular events such as myocardial infarction and stroke, as well as the occurrence of restenosis following vascular interventions, can be significantly reduced.

U.S. Pat. No. 4,835,147 to Roberts demonstrated that administration of DHEA or its therapeutically acceptable salts to individuals ameliorated symptoms of prostatic hypertrophy, certain symptoms of menopause, particularly those related to nervous system dysfunction, and of psychosexual dysfunction, symptoms such as inhibited sexual desire, inhibited sexual excitement and inhibited orgasm.

Other widely varying medical uses for DHEA have been reported. U.S. Pat. No. 4,628,052, issued to Peat, reports using either an oral or topical preparation of DHEA to treat rheumatoid arthritis, osteo-arthritis and arthritis associated with psoriasis and with lupus and other auto-immune diseases, and also for treating non-specific joint pain associated with stress or incidental to other ailments.

DHEA compounds have also been established to have a beneficial effect as an anti-diabetic agent. See U.S. Pat. No. 4,518,595 to Coleman et al.

In the medical literature, many favorable reports of medical benefits to individuals due to increased levels of DHEA and its sulfate ester, DHEA-S, have been reported as well. *Geriatrics* 37:157 (1982) stated that DHEA was a "miracle" drug, which may prevent obesity, aging, diabetes mellitus and heart disease. Barrett-Conner et al. produced studies which revealed an inverse relationship between cardiovascular death and serum DHEA-S levels in adult men. *N. Engl. J. Med.* 315:1519 (1986). Arad et al. in *Arteriosclerosis* 9:159 (1989) and Gordon et al. in *J. Clin. Invest* 82:712 (1988) both describe the reduction of atherosclerosis plaque formation by DHEA.

One of the most important uses of DHEA has been to improve the immune response in human beings. U.S. Pat. No. 5,077,284, issued to Loria et al., describes the administration of DHEA, either orally or by subcutaneous injection, to provide very high levels of protection against viral, bacterial, fungal or parasitic infections in immuno-compromised animals and humans. The experimental animal data, described by Loria et al., demonstrated that in infection (100,000 plaque forming units/animal) of a human coxsackievirus B4 strain, which causes mortality in about 90% of infected animals, mortality was reduced to 37% when animals were treated with DHEA. Moreover, Loria et al. demonstrated that administration of DHEA induced an 80% elevation in the number of antibody forming cells within the animal. In virus infected and DHEA treated animals, there was also an elevation in the number of monocyte cells, the particular white blood cells associated with a resistance to coxsackievirus infection. This elevation was not observed in uninfected animals that were treated with DHEA. This observation demonstrates that DHEA can be used to up-regulate the host immune response to virus infection, by increasing the number of antibody forming cells, elevating the number of white blood cells associated with resistance to virus infection and markedly reducing virus induced mortality.

Although DHEA is the most abundantly produced adrenal steroid and serum concentrations of its sulfate ester, DHEA sulfate (DHEA-S), are approximately 20 fold higher than those of any other circulating steroid hormone, levels of this hormone begin to decline within individuals during the second decade of life, reaching 5% of the original level in the elderly.

Peak serum DHEA and DHEA-S levels occur when a patient is approximately 25 years old and decline over the ensuing decades. Ohrentreich et al. found that mean DHEA-S levels and ranges for adult men were as follows: Ages 25–29 (3320 ng/ml); ages 45–49 (1910 ng/ml); ages 65–69 (830 ng/ml). See *J. Clin. Endocrinol. Metab.*, 59:551 (1984). Similar age related decline in serum DHEA-S levels were found to occur in women. Correspondingly, the incidence of cardiovascular disease in human beings increases with age, thus suggesting an epidemiological relationship between serum DHEA and DHEA-S levels in cardiovascular disease. In Barrett-Conner et al., supra, the base line DHEA-S levels of 242 middle aged men (ages ranging between 50 and 79 years) was compared to the subsequent 12 year mortality rate of the men from any cause, from cardiovascular disease, and from ischemic heart disease. DHEA-S levels were significantly lower in men with a history of heart disease compared to those without. In men with no history of heart disease, the age-adjusted relative risk associated with DHEA-S levels below 140 µg/dl was 1.5 (p NS) for death from any cause, 3.3 (p<0.05) for deaths from cardiovascular disease, and 3.2 (p<0.05) for deaths from ischemic heart disease. An increase in DHEA-S level of 100 µg/L had a 48% reduction in mortality (adjusted for other risk factors) from cardiovascular disease (p<0.05).

Further Eich et al. supra, demonstrated that treating human beings with pharmacological quantities of DHEA resulted in increased serum levels of DHEA and DHEA-S. Eich et al. performed in vivo experiments using a test group of 10 male human being subjects. In these experiments, DHEA was administered in a double-blind placebo controlled trial in an amount of 300 mg of DHEA per day in the form of 100 mg capsules taken orally 3 times a day. The study found that the initial baseline serum DHEA prior to conducting the experiment was 5.83+/−3.9 ng/ml, and the mean serum DHEA during the second week of investigation for the placebo group was 5.58+/−4.1 ng/ml. The mean serum DHEA for the treated group during the second week investigation was 28.7+/−13.9 ng/ml. In addition, the baseline serum DHEA-S was 316.2 μg/dl and during the second week, the mean serum DHEA-S level was 260.5+/−56.7 μg/dl in the placebo group, and 1451.9+/−56.7 μg/dl in the DHEA group. Elevation of serum DHEA-S levels when a patient is receiving only supplemental DHEA suggested that DHEA-S serves as a storage pool for DHEA, which is the active form of the hormone. The rate of platelet aggregation for the human subjects participating in this study was examined prior to treatment with supplemental DHEA and was again tested on three different occasions during the second week of an investigation. Four of the five test subjects who received the DHEA supplement demonstrated a slower rate of aggregation and a requirement for higher concentration of arachidonic acid to initiate aggregation. Thus, the elevated serum DHEA level slowed platelet aggregation which can significantly reduce the incidence of morbidity and mortality from vascular events such as myocardial infarction and stroke.

SUMMARY OF THE INVENTION

The present invention provides a method for enhancing or restoring DHEA in a living human being. Because DHEA is a naturally occurring steroid, it has been found that endogenous production of the hormone may be stimulated by several methods, without the use of exogenous dietary supplements or pharmaceutical preparations containing DHEA, its sulfate ester DHEA-S, or salts thereof.

One object of the invention is to provide a method for elevating serum DHEA levels in an individual through the use of regularly administered topical treatments of an ointment or other pharmaceutical preparation containing the steroid progesterone. The progesterone ointment is applied to less hirsute regions of the body, preferably the backside of the abdomen, the buttocks, or the inside of the thighs; or the scrotum on males or the breasts of females. The progesterone cream should be applied in a pharmacologically active amount, on a daily basis for a sufficient period of time, to elevate the patient's serum DHEA levels. The time period for this treatment is minimally several weeks.

Serum DHEA levels in human beings may also be raised without the use of dietary supplements or pharmaceuticals by applying electrical stimulation to specific epidermal points of the individual's body for a period of time daily to raise DHEA levels. The electrical stimulation is applied to specific locations on the individual's body which correspond to twelve well known acupuncture points. The electrical stimulation is applied to these acupuncture points on a daily basis over a number of weeks to achieve a significant increase in serum DHEA levels within the patient. Preferably, the electrical stimulation is applied for a minimum period of two to four weeks.

It has been found that the greatest increase in serum DHEA levels occurred in patients treated with daily electrical stimulation applied to the specific acupuncture points combined with daily topical application of a pharmaceutical preparation containing progesterone. This combination of electrical stimulation and progesterone cream, applied to an individual on a daily basis for a period of several weeks was effective in elevating DHEA levels in patient's serum by 100% to 300%.

DETAILED DESCRIPTION OF THE INVENTION

It has been found that DHEA levels may be raised in human beings without the application of exogenous supplements of DHEA, DHEA-S, or their corresponding salts. Topical treatments consisting of electrical stimulation and/or ointments containing the steroid progesterone, applied on a daily basis for a period of time to specific locations of the patient's body, have been surprisingly and unexpectedly found to increase production of DHEA. Preferably, this treatment should be continued for a minimum of two weeks and may take as long as twelve weeks before a rise in serum DHEA is detected. Stimulating biosynthesis of DHEA within the body is advantageous over the heretofore known methods of raising serum DHEA levels which consisted of DHEA, DHEA-S, or salts thereof, taken either parenterally, intravenously, subcutaneously or transdermally. Clinical studies of treatments involving administration of DHEA, its esters, or salts thereof, have been associated with undesirable side effects. These side effects include mild androgenic effects and hirsutism. See W. Regelson et al., *New York Academy of Sciences*, 518:260 (1988). Side effects from the ingestion of DHEA, and other undesirable consequences involving the method of DHEA administration, can be avoided with the method of the present invention. No side effects have been detected from utilization of the present invention to raise DHEA levels in patient's blood.

Each of the two apparatus herein described, or topical application of a pharmaceutical preparation containing progesterone, either alone or in combination with each other, have been found to raise serum DHEA levels in human beings.

To illustrate performance of the method of the present invention, the apparatus as described in U.S. Pat. No. 5,109,847, the entire disclosure of which is hereby incorporated by reference, is used to increase serum DHEA levels in patients by placing electrodes at specific points on an individual's body. The treatments from this electronic stimulation preferably are for five minutes daily at each point on the body where the electrodes are placed. DHEA serum levels were found to be increased after two weeks of this treatment.

A time varying electrical potential stimulus is applied between the first electrode and the second electrode of this device. The electrical stimulus comprises a low level voltage (typically yielding a current of less than 4 milliamperes) pulse train of relatively high frequency, i.e. between 12 and 20 kHz, modulated in amplitude by a relatively low frequency wave in the range of 8 to 20 Hz. The low frequency wave is preferably non-symmetrical, characterized by 3:1 duty cycle, being on three quarters of the time and off one quarter of the recurring period. By way of example only, the high frequency pulse may occur at a 15 kHz rate at about a 4.0 ma level, while being subject to a 15 Hz modulation with a 3:1 duty factor.

FIGS. 6A–6E present the various components of a complex waveform of the present invention. More particularly, in starting with FIG. 6A, a graphical representation is provided of a carrier frequency for one specific time segment. In this representation, the carrier frequency equals 15 kHz. The amplitude is volts (DC) and a duty cycle of 50%. The waveform contains 25 bursts of 15 pulses for each burst. The period for each burst is 2 milliseconds and the period for each pulse is 66.7 microseconds. For each, the burst and the pulse, the duty cycle is 50% on time.

Figure 1:
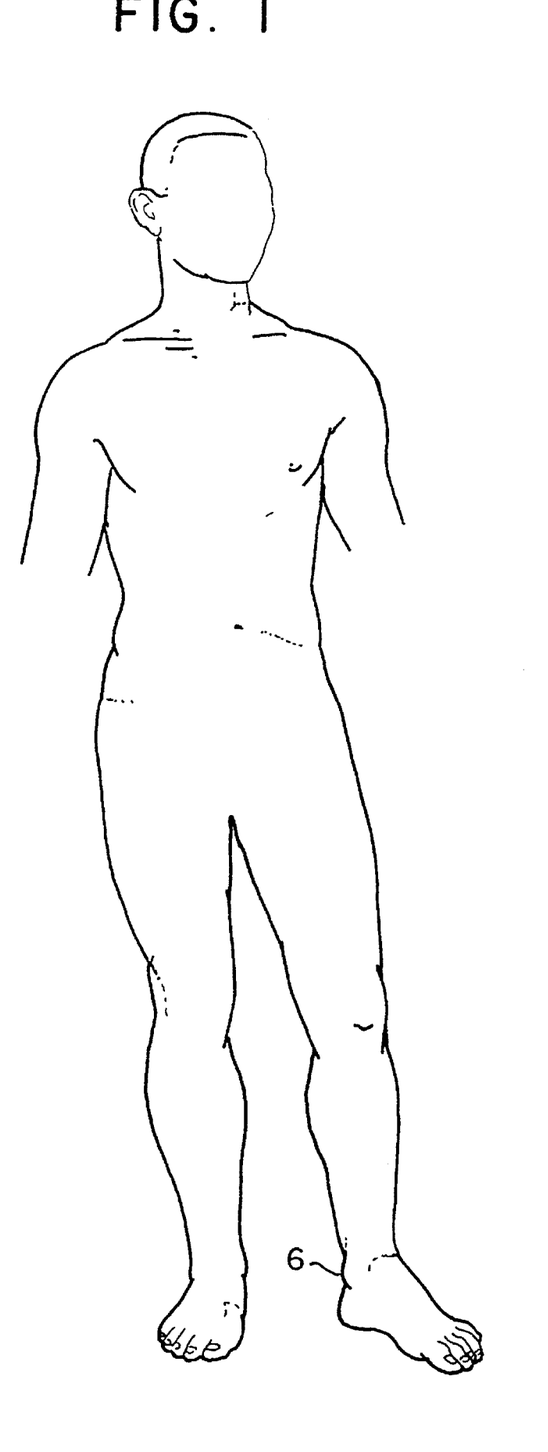
FIG. 1 is a frontal sketch of a human being illustrating three acupuncture points included in the Ring of Fire.
Figure 2:
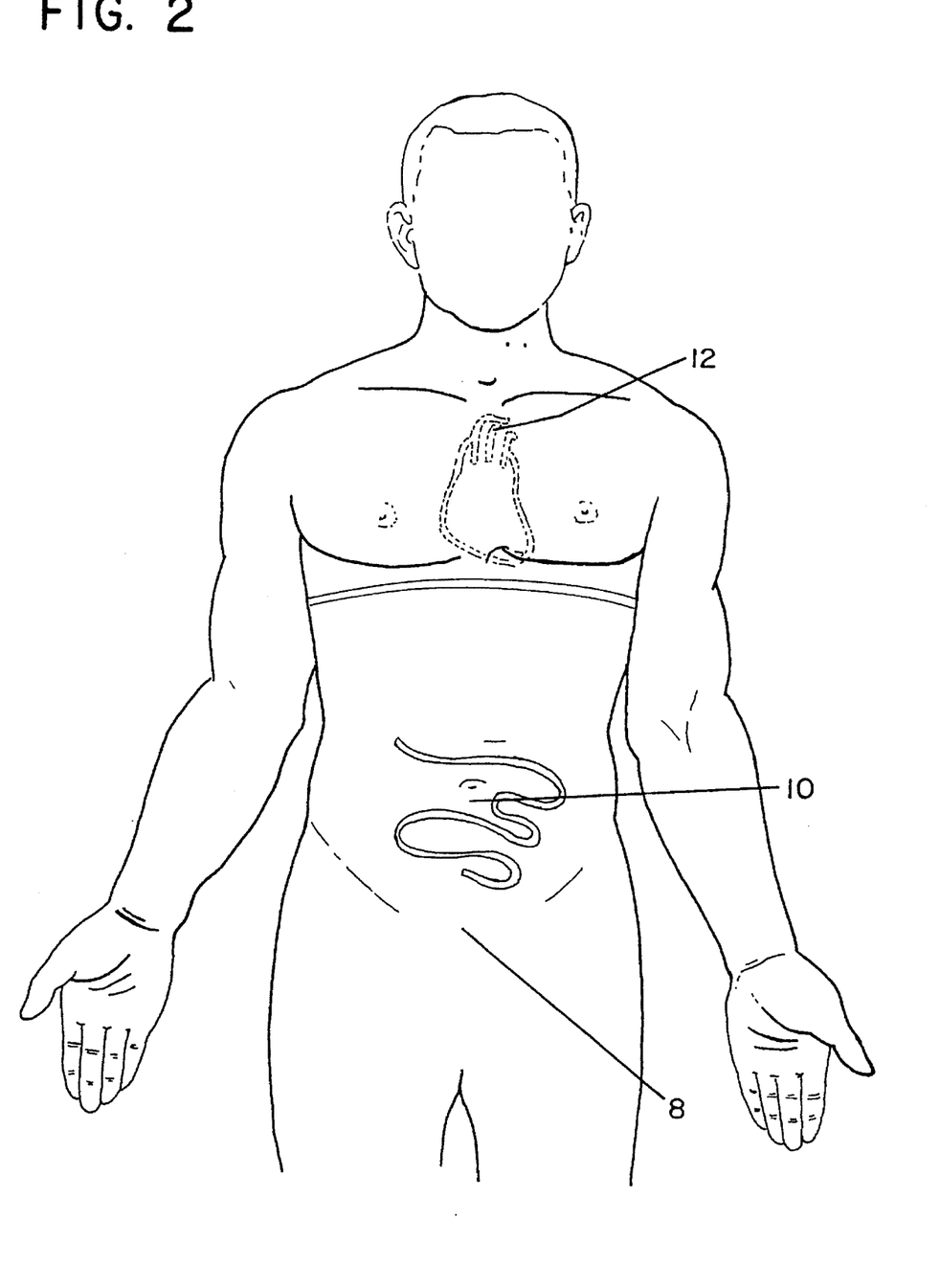
FIG. 2 is a frontal sketch of a human being illustrating one acupuncture point included in the Ring of Fire.
Figure 3:
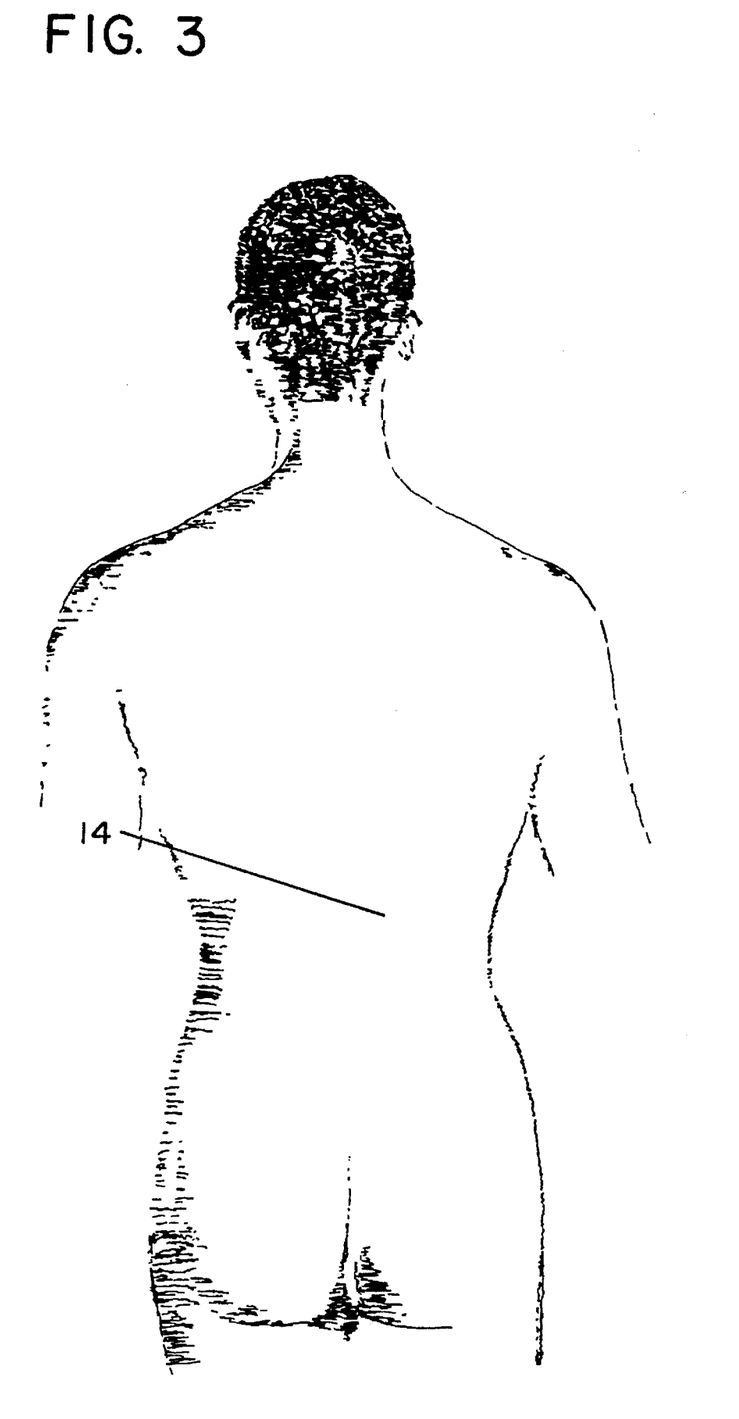
FIG. 3 is a left profile sketch of a human being illustrating two acupuncture points included in the Ring of Fire.
Figure 4:
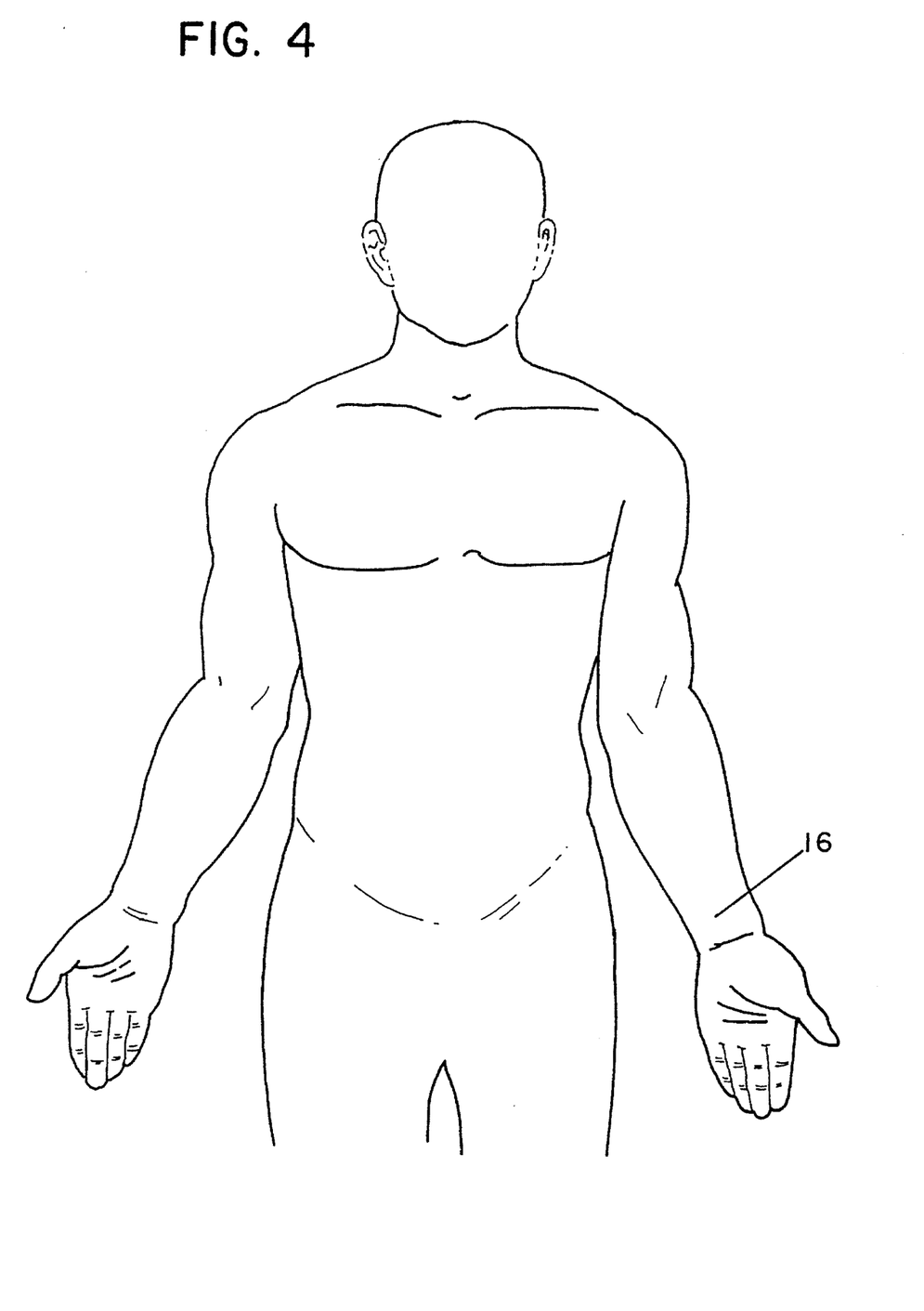
FIG. 4 is a back profile sketch of a human being illustrating one acupuncture point included in the Ring of Fire.
Figure 5:
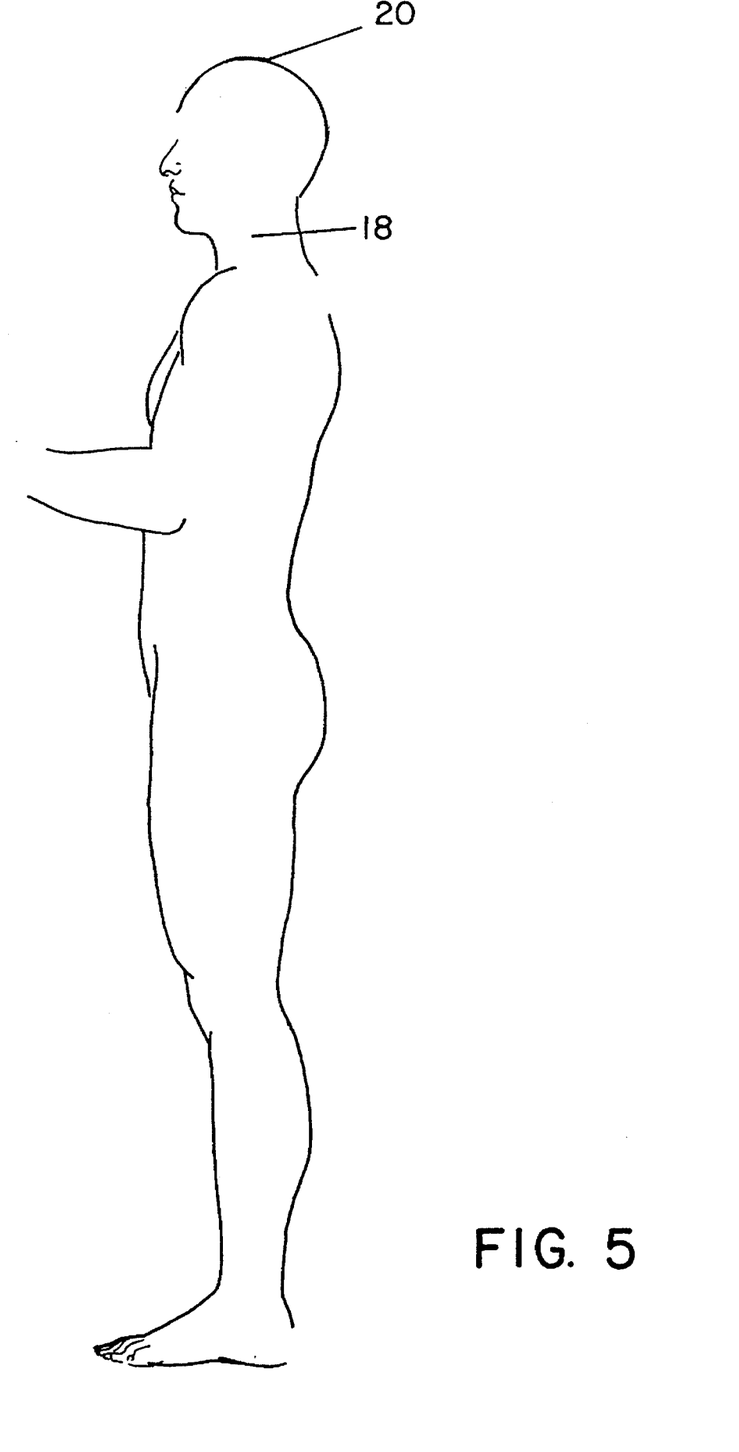
FIG. 5 is a frontal sketch of a human being illustrating one acupuncture point included in the Ring of Fire.
Figure 6A:
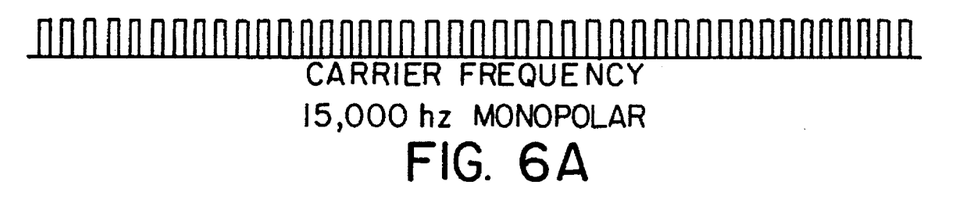
FIG. 6 is a representation of a sample waveform utilized in the present invention.
Figure 6B:
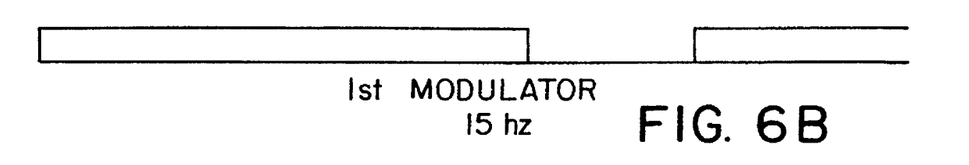
Figure 6C:
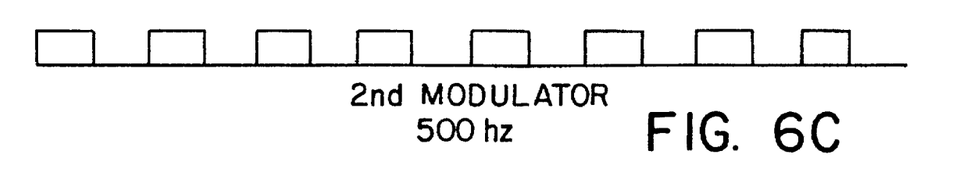
Figure 6D:
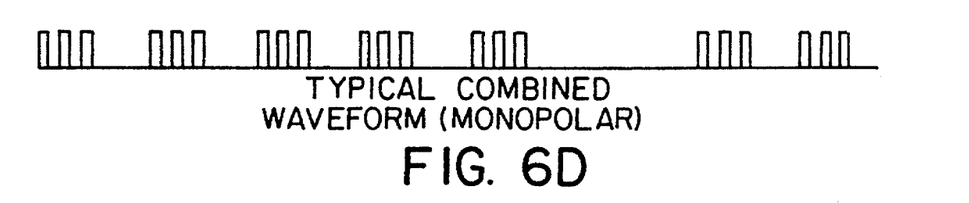

FIG. 6B presents the first modulation to the carrier frequency. In this example, the first modulation has a frequency of 15 Hz and a duty cycle of 0.75. The second modulation is depicted in FIG. 60. The second modulation has a frequency of 500 Hz and a 50% duty cycle. FIG. 6D depicts the waveform combining the components shown in FIGS. 6A–6C.

The complex waveforms of the present invention may be generated with sinusoidal, sawtooth, hyperbolic, or other wave shapes; for clarity, the waveforms presented in FIG. 6 and further discussed below have been exemplified by a simple square wave.

A cycle for the waveform will consist of 50 milliseconds "on" time in which the pulses for that frequency combination are generated and then there will be an "off" time of 16.7 milliseconds.

Figure 6E:
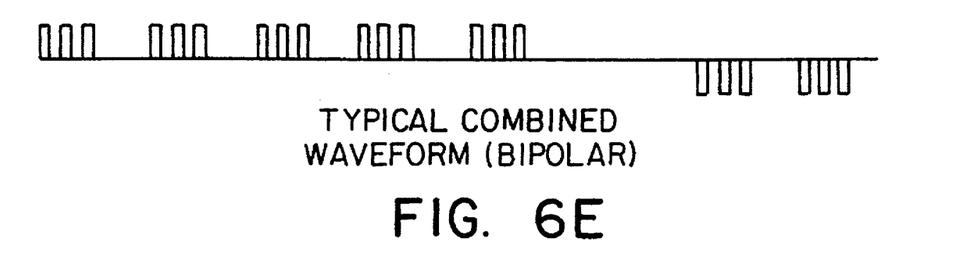

Finally, in FIG. 6E, a complex waveform according to the present invention is provided wherein the polarity of the output is switched from positive to negative on a periodic basis, e.g., 67 milliseconds. This is contrasted with the waveform of FIG. 6D in which the polarity remains positive throughout the cycle; the pulse DC waveform of FIG. 6D waveform of FIG. 6D is considered a monopolar output while the output depicted in FIG. 6E is considered bipolar.

For purposes of rough approximation, the energy dissipation in using an electrical stimulator according to the present invention is represented by the area under the pulses depicted in FIG. 6D. It can, therefore, be recognized that by adding the second modulation, having a 50% duty cycle, results in a 50% decrease in power dissipation.

The circuit is presently provided with one of the following frequency combinations but not limited to:

(1) 15 Hz, 500 Hz, 15,000 Hz - monopolar;
(2) 15 Hz, 500 Hz, 15,000 Hz - bipolar (7.5 Hz);
(3) 15 Hz, 500 Hz, 60,000 Hz - monopolar; or
(4) 15 Hz, 4,000 Hz, 60,000 Hz - monopolar.

Figure 7:
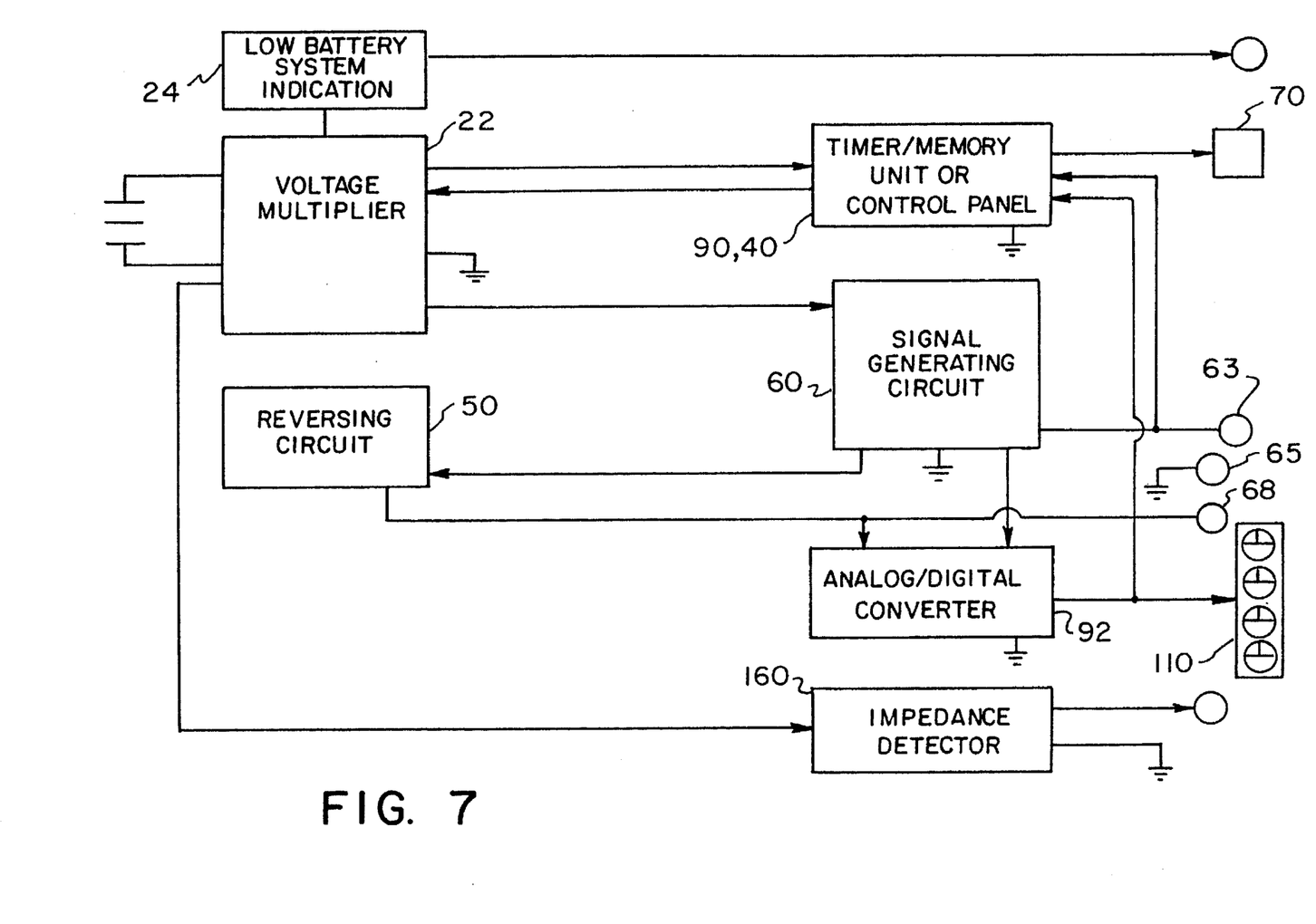
FIG. 7 is a block diagram of an apparatus for generating the waveform depicted in FIG. 6.

FIG. 7 shows the functional elements of an electrical stimulator used in the present invention. The power source to the electrical stimulator will either be a battery having nominal 9 volt terminal voltage or some rectified and properly transformed line (AC) power source. The battery provides the basic DC power source for generating the complex waveform. This is channeled and controlled by the voltage multiplier 22. The output of a voltage multiplier 22, which is between 27–40 volts, is fed to signal generating circuit 60 which is the oscillating circuit that converts the constant DC output into the complex waveform having the desired characteristics.

The specific constant current and current limited waveform generated by signal generating circuit 60 is pre-set by entering the various frequency settings for the two modulations, and the carrier. This may be entered manually through adjusting the settings on control panel 90. Alternatively, these settings may be stored in digital memory 40 as previously set values. The actual output of this system is regulated by monitor 70 which then provides the system output on a display, via control panel 90, or a memory value for subsequently retrieval from memory 40.

The signal generating circuit 60 receives the voltage of 27 v to 40 v from the voltage multiplier. Within the signal generating circuit 60, the voltage branches off into a carrier frequency and two modulation frequencies. An example of the branching of the waveform is described in FIG. 6.

In FIG. 7, the system supports two separate electrodes for placement on the patient. Electrode 63 represents the positive terminal as generated by signal generating circuit 60. The second electrode 65, is grounded within the circuit. For operation applying a bipolar waveform the electrodes are connected to terminals 65 and 68, respectively. Terminal 68 is the output from reversing circuit 50, which may be present and which acts to flip the signal generating circuit pursuant to preset timing constraints.

The following ancillary systems are also present in this circuit. The low battery and system on indicator 24 which monitors the battery output via voltage multiplier 22 generates an alarm signal when battery output voltage drops below the preset limit, say 7.0 volts. It also shuts the system down if the output voltage falls below the present limit of approximately 6.0 volts.

The analog/digital converter 92 converts the signal from the signal generating circuit 60 so that the patient can read it. The analog/digital converter 92 reads the level of output and converts it to the appropriate signal for the four gate integrated circuit which uses that signal to turn on the appropriate sequence of four LEDs 110.

Finally, the impedance detector 160 is used to determine if the system is being used on a person (as opposed to someone just running the system without attaching it to a person).

Figure 8:
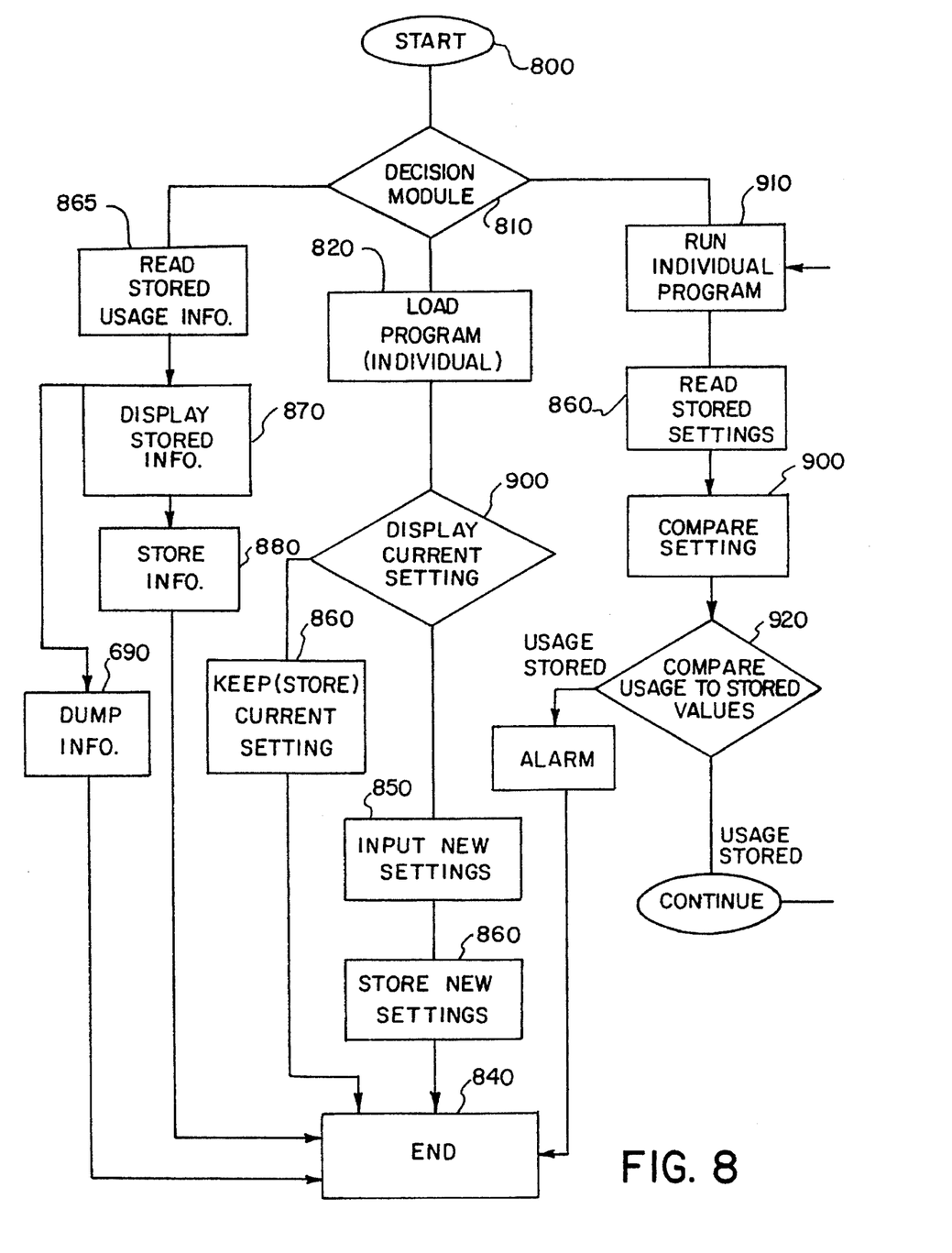
FIG. 8 is a logic flow chart of a data processing program controlling the operation of the apparatus of FIG. 7.

Referring now to FIG. 8, which is a flow chart of the timer unit 90 which the apparatus will use to monitor usage by the patient. This program will prevent the patient from misusing the electrical stimulator apparatus and will allow the physician to set an individual treatment program and to monitor the patient's compliance to the set program.

The timer unit 90 will allow the therapist to set the number of days the system is to be used, the number of times per day the system will be used and the time duration for each use.

The program will start 800 with an Origination Decision Module 810. The Origination Decision Module 810 will give the therapist three choices for use. If the Individualized Program 820 pathway is chosen, the timer unit will load the Individualized Program 820. Then the Individualized Program 820 will begin with a display showing the Current Setting 900, for each of the parameters (i.e., the number of days of use, the number of times per day of use and the length of time for each use). Next the program will ask the therapist whether he wants to keep the Current Settings 900, or Input New Settings 850. If the therapist wishes to use the same settings as are already registered in the program, the Individualized Program 820 will Store 860 the values and will End 840. However, if the therapist wishes to change the settings, the program will proceed to the Change Input Values 850 module in which the computer will ask the therapist for the new values for the settings. Then the computer will Store 860 the new values and will End 840.

Another selection which a therapist may make at the Origination Decision Module 810 is to read the stored information from the patient's system. If the therapist decides to access the Read Stored Results 865 module, the Setting and Use information will be displayed 870, and the therapist will decide whether to store the patient information in the Patient Storage Module 880, or else it will Dump the information 890 and it will End 840.

A final selection which the therapist may access through the Origination Decision Module 810, is actually to use the system. If this choice is the inputted selection, the Run Timed Program 910 will be initialized. The Run Timed Program 910 will read the stored 860 values. Then the program will Check 920 the Stored 860 values against the Current Running Settings 900 which is the values of the Run Timed Program 910 for this usage of the system. If the Current Running Settings 900 for the number of days of use is greater than the Stored 860 values, the program will End 840 without the system being turned on. Next, the Run Timed Program 910 will check the value of the Stored 860 values for the number of uses for a given day and if the Current Running Settings 900 is greater than the Stored 860 values for number of uses for a day, the system will End 840 for that day and the system will not be able to be used until the next day. Finally, as the system is being use, a Running Time Clock will be compared to the Run Timed Program 910 and when the Current Running Settings in 900 is greater than the Stored 860 values for the length of time for that session, the system will End 840 for that session and the system will not be able to be used until the next session period.

The Liss Cranial Stimulator (MEDI Consultants, Inc., 265 Vreeland Avenue, Paterson, N.J.) is a commercially available device which provides an electric signal equivalent to the corresponding signal described above. The Liss Cranial Stimulator has been previously shown to reduce symptoms of depression, anxiety and insomnia, when the electric signal from the Liss Cranial Stimulator was applied bitemporally to individuals showing signs of these problems. The device is the preferred electrical stimulator which produces a high frequency electrical wave bearing a low frequency amplitude modulation to the pair of electrodes used in the present invention.

The Liss Cranial Stimulator was ineffective, however, in raising DHEA serum levels in patients when the device was used bitemporally. It is only through the use of the Liss Cranial Stimulator in the heretofore unknown method of applying electrical stimulation to the set of acupuncture points known as the Ring of Fire whereby serum DHEA levels were found to be increased.

Another form of electric stimulation of individuals has been found to increase serum DHEA levels in individuals. This stimulation may be applied by use of an apparatus capable of delivering a very high frequency electrical stimulus, e.g. up to 300 GHz at an energy level of up to 1 microvolt. This apparatus, referred to as the GigaTENS™ Electrical Stimulator, is used to provide the proper electrical stimulation to the individual to raise DHEA serum levels by placing the electrodes from the device on specific points of an individual's body, and applying a very high frequency electrical stimulus, e.g. up to 300 GHz at a power level of $10^{-9}$ w/cm$^2$, and preferably at 52 to 78 GHz at an electrical power of $10^{-9}$ w/cm$^2$, in a sequential manner to each of the specific points, corresponding to the Ring of Fire, on the individual's body for a period of about 3 minutes per day on a daily basis for a period of at least two weeks.

These specific points on the individual's body preferably correspond to 12 specific acupuncture points, hereinafter defined as the "Ring of Fire". As FIGS. 1–5 illustrate, these 12 points correspond to well known acupuncture points located in various places on the body. The position of these various points are roughly illustrated in FIGS. 1–5 and correspond to the acupuncture points of Kidney (K3) 6; Conception Vessel (CV2) 8; Conception Vessel (CV6) 10; Conception Vessel (CV18) 12; Bladder (B22) 14 which is a bilateral point; Master of the Heart (MH6) 16 which is a bilateral point; Large Intestine (LI18) 18 which is a bilateral point; and Governing Vessel (GV20) 20. Conception Vessel point CV1 is not pictured, but is located midway between the anus and the genitals. Although these acupuncture points are well known in Chinese acupuncture literature, this combination of points has not been previously described and it has been surprisingly and unexpectedly discovered in accordance with the invention that this combination of acupuncture points, i.e. the Ring of Fire, can be electrically stimulated to raise DHEA serum levels in individuals.

In accordance with the invention, it has also been surprisingly and unexpectedly discovered that topical applications of an ointment or cream containing the steroid progesterone, preferably 3% progesterone by weight, applied twice a day to the skin for six months, can raise DHEA levels in an individual. The amount of the ointment or cream to be applied which is sufficient to be effective for the indicated activity will vary with the individual being treated and is ultimately at the discretion of the medical practitioner. The factors to be considered include the exact nature of the formulation, the individual's body weight, surface area, age and general condition, and the particular formulation to be administered. However, a suitable effective dose is in the range of 30–80 mg, preferably applied twice a day to an individual's body as previously described.

EXAMPLES

The DHEA serum levels of over 500 individuals were initially determined prior to DHEA enhancement by the present invention. All DHEA serum measurements of samples of blood taken from subjects were performed by Nichols Labs of Capistrano, Calif. All DHEA serum measurements herein are accurate to within +/–4 percent. From these measurements, it appears that the optimal DHEA serum levels for men is in the range of 750–1250 ng/dl, with a mean value for the men tested of 625 ng/dl; and for women the optimal DHEA serum level ranges between 550–980 ng/dl with a mean value for the women tested of 490 ng/dl. It was noted that exceptionally healthy persons had serum DHEA levels at the upper end of the range determined, independent of the age of the individual tested. One 59 year old female individual in the sample had a DHEA level of 658 ng/dl of DHEA. Overall, the healthiest individuals in this sample had DHEA levels 20% or more above the mean. In fact, all patients (over 500) treated at the Shealy Institute (1328 E. Evergreen, Springfield, Mo.) over a period of three years who evidenced any type of illness had DHEA serum levels well below the appropriate mean DHEA serum levels for their sex.

In one set of trials with 5 individuals, the Liss Cranial Electrical stimulator was applied for three minutes to each of the 12 specific acupuncture points in the Ring of Fire, as illustrated in FIGS. 1–5. In these individuals, serum DHEA levels increased by 50% to 60% after four to eight weeks of treatment, three minutes a day. The results of this increase can be seen in Table 1.

TABLE 1

ENHANCEMENT OF SERUM DHEA LEVELS VIA APPLICATION OF LISS CRANIAL ELECTRICAL STIMULATION TO THE RING OF FIRE

| Sex | Age | DHEA BEFORE | DHEA AFTER* |
|---|---|---|---|
| F | 47 | 184 | 286 (4 wk.) |
|   |    |     | 327 (8 wk.) |
| F | 51 | 79  | 207 |
| M | 30 | 180 | 275 |
| F | 79 | 14  | 130 |
| F | 42 | 224 | 330 |

*Measurement taken after 8 weeks of treatment, unless otherwise indicated.

In a further study, the GigaTENS™ Electrical Stimulator was applied for three minutes daily to each acupuncture point in the Ring of Fire for up to 12 weeks in six individuals. In six subjects in the study, DHEA levels increased by 50 to 100%. The results of this are shown in Table 2. Two individuals who had shown enhancements in their DHEA serum levels stopped using this GigaTENS™ Stimulator after four weeks, and their DHEA levels declined again over the next month to their initial value.

TABLE 2

ENHANCEMENT OF SERUM DHEA VIA APPLICATION OF GigaTENS™ TO THE RING OF FIRE

| SEX | AGE | DHEA BEFORE | DHEA AFTER |
|---|---|---|---|
| M | 60 | 295 | 440 |
| M | 42 | 459 | 692 |
| M | 69 | 251 | 376 |
| F | 30 | 170 | 260 |
| F | 50 | 130 | 225 |
| M | 55 | 238 | 375 |

In accordance with the invention it has been determined that topical or local applications of the use of an ointment or cream containing progesterone, preferably 3% by weight, applied twice a day to the skin for six months, could raise DHEA levels in the individual. The ointment was applied to less hirsute regions of the patient's body as previously described. The amount of the ointment or cream to be applied required to be effective for the indicated activity will, of course, vary with the individual being treated and is ultimately at the discretion of the medical practitioner. The factors to be considered include the exact nature of the formulation, the individual's body weight, surface area, age and general condition, and the particular formulation to be administered. However, a suitable effective dose is in the range of one quarter teaspoon applied twice per day to one quarter teaspoon applied four times daily. In a trial utilizing the application of a topical progesterone cream on seven individuals by placing the ointment in the individuals twice a day for six months in the manner previously described, seven individuals experienced an increase in their DHEA levels of 50 to 100%. These results are shown in Table 3.

TABLE 3

DHEA SERUM LEVEL ENHANCEMENT VIA APPLICATION OF PROGESTERONE CREAM

| SEX | AGE | DHEA BEFORE | DHEA AFTER* |
|---|---|---|---|
| M | 64 | 130 | 182 |
| M | 58 | 134 | 190 |
| M | 50 | 105 | 197 |
| M | 68 | 120 | 214 |
| M | 59 | 225 | 440 |
| M | 48 | 210 | 335 |
| M | 51 | 180 | 300 |

*Measurement taken after 6 months of treatment.

To obtain the best results in stimulating natural production of DHEA in patients it is preferred to utilize a combination of twice daily application of a progesterone cream, formulated as previously described, together with electrical stimulation of the bladder 22 acupuncture points by the Liss Cranial Stimulator for 30 minutes daily and stimulation to the remainder of the Ring of Fire points with the GigaTENS™ Stimulator for three minutes each daily for two weeks, with continuing use of the Liss Cranial Stimulator at all of the Ring of Fire points six days per week and then the GigaTENS™ the remaining one day per week on all points in the Ring of Fire for the next ten weeks. In the three individuals in the study, DHEA levels increased by 100 to 300%. The results are shown in Table 4.

TABLE 4

ENHANCEMENT OF SERUM DHEA LEVELS VIA APPLICATION OF GigaTENS™ + LISS CRANIAL ELECTRICAL STIMULATION PROGESTERONE

| SEX | AGE | DHEA BEFORE | DHEA AFTER |
|---|---|---|---|
| M | 61 | 300 | 914 |
| M | 55 | 238 | 475 |
| M | 30 | 195 | 390 |

As discussed supra, Loria et al. demonstrated the strong correlation between enhanced immune response and serum DHEA levels. Loria, et al, stated that increased serum DHEA levels could provide a very high amount of protection against a host of pathogenic viral, bacterial, fungal infections, including opportunistic infections. It was also postulated that raising levels of DHEA in patient's serum is of value in the treatment of immuno compromised individuals suffering from AIDS or those infected with the HIV virus showing the AIDS related complex (ARC).

Eich et. al, supra, demonstrated that elevated levels of DHEA and DHEA-S in patient's serum resulted in lower rates of platelet aggregation. It is well known that reducing the rate of platelet aggregation has significant health benefits, including, but not limited to, reduction in the incidence of mortality from vascular events such as stroke, and also reduces the occurrence of restenosis following vascular interventions. Therefore, by raising serum DHEA levels in individuals via treatment utilizing the methods of the current invention, health benefits are expected.

It is understood that the invention is not confined to the particular embodiments set forth herein as illustrative, but embraces all such modifications thereof as come within the scope of the following claims.

What is claimed is:

1. A method of raising serum DHEA levels in an individual comprising the steps of:

(a) applying electrodes sequentially to at least one acupuncture points selected from a Ring of Fire acupuncture points of the individual's body; and (b) applying a high frequency of at least 1 kHz electrical stimulus bearing a low frequency amplitude modulation to the electrodes at each selected acupuncture point repetitively over a period of time sufficient to result in stimulation of endogenous production of DHEA within the individual.

2. The method of claim 1 wherein the electrical stimulation is applied for a period of time of approximately five minutes at each of the acupuncture points at least once per day for a period of at least fourteen days.

3. The method of claim 2 wherein the frequency of the high frequency electrical stimulation is in the range of 12–20 kHz, modulated by a low frequency amplitude modulation in the range of 8–20 Hz, and wherein the current applied to the individual by the electrical stimulation does not exceed about 4.0 milliamperes.

4. The method of claim 3 wherein the amplitude of the modulation is non-symmetrical.

5. The method of claim 1 wherein the electrical stimulus is at a frequency of 52 to 78 GHz and further comprises a power level of $10^{-9}$ w/cm$^2$.

6. A method of raising serum DHEA levels in an individual comprising the steps of:

(a) applying first electrodes sequentially to at least one acupuncture points selected from a Ring of Fire acupuncture points of the individual's body;

(b) applying a high frequency electrical stimulus bearing a low frequency amplitude modulation to the first electrodes at each acupuncture point;

(c) applying second electrodes sequentially to at least one of the Ring of Fire acupuncture points of the individual's body;

(d) applying a high frequency electrical stimulus to the second electrodes at each acupuncture point;

(e) topically applying a pharmacologically active amount of a pharmaceutical preparation containing progesterone to the individual; and (f) repeating steps (a) through (e) repetitively over a period of time sufficient to result in stimulation of endogenous production of DHEA within the individual.

7. The method of claim 6 wherein for the first two weeks of treatment, the first electrodes are applied on the Bladder points of the Ring of Fire for a minimum of three minutes at least once per day while applying a high frequency electrical stimulus bearing a low frequency amplitude modulation to the first electrodes at the Bladder points, and the second electrodes are applied on the remaining eleven specific acupuncture points of the Ring of Fire for a minimum of three minutes at least once per day while applying a high frequency electrical stimulus to the second electrodes at each acupuncture point, and wherein for the remaining duration of treatment, the first electrodes are applied on all twelve specific acupuncture points of the Ring of Fire for a minimum of three minutes at least once per day while applying a high frequency electrical stimulus bearing a low frequency amplitude modulation to the first electrodes at each acupuncture point, and the second electrodes are applied on all twelve specific acupuncture points of the Ring of Fire for a minimum of three minutes at least once per day while applying a high frequency electrical stimulus to the second electrodes at each acupuncture point.

8. The method of claim 7 wherein the step of topically applying the pharmaceutical preparation containing progesterone further comprises applying the preparation at least once per day.

9. A method of raising serum DHEA levels in an individual comprising the steps of:

(a) applying electrodes, the electrodes attached to an electrical generator, to six sets of acupuncture points sequentially at each set of acupuncture points; and (b) applying a moderately high frequency from the electrical generator to the electrodes of at least 1 kHz having an electrical amplitude which does not exceed two milliamperes, to stimulate endogenous production of DHEA within the individual.

10. The method of claim 9 wherein the step of applying the electrical stimulus further comprises applying the electrical stimulus for a period of five minutes to the electrodes.

11. A method of raising serum DHEA levels in an individual comprising the steps of:

(a) applying electrodes sequentially to at least one acupuncture point selected from a Ring of Fire acupuncture point on an individual's body;

(b) applying an electrical stimulus having a frequency of 52–300 GHz sequentially to the electrodes at each of the selected Ring of Fire acupuncture points; and (c) continuing the electrical stimulus for approximately three minutes at each point to stimulate endogenous production of DHEA within the individual.

12. The method of claim 1 wherein the amplitude of current does not exceed 1 microvolt on any one acupuncture point.

\* \* \* \* \*